US006955824B1

(12) United States Patent
Hallworth

(10) Patent No.: US 6,955,824 B1
(45) Date of Patent: *Oct. 18, 2005

(54) INHALATION COMPOSITION CONTAINING LACTOSE PELLETS

(75) Inventor: Gerald Wynn Hallworth, Ware (GB)

(73) Assignee: Glaxo Group Limited, Greenford (GB)

(*) Notice: Subject to any disclaimer, the term of this patent is extended or adjusted under 35 U.S.C. 154(b) by 857 days.

This patent is subject to a terminal disclaimer.

(21) Appl. No.: 09/651,083

(22) Filed: Aug. 30, 2000

Related U.S. Application Data

(63) Continuation of application No. 08/702,700, filed as application No. PCT/EP95/00917 on Mar. 13, 1995, now Pat. No. 6,183,782.

(30) Foreign Application Priority Data

Mar. 15, 1994 (GB) .................................. 9404945

(51) Int. Cl.⁷ .............................................. A61K 9/16
(52) U.S. Cl. ...................... 424/490; 424/45; 424/46; 424/489
(58) Field of Search ................. 424/489, 490, 424/45, 470, 46

(56) References Cited

U.S. PATENT DOCUMENTS

| 2,897,119 A | 7/1959 | Dunn ........................ 167/81 |
| 3,341,415 A | 9/1967 | Scott ......................... 167/82 |
| 3,957,965 A | 5/1976 | Hartley et al. ............. 424/14 |
| 4,161,516 A | 7/1979 | Bell ........................... 424/14 |
| 4,605,552 A | 8/1986 | Fritschi |
| 5,143,126 A | 9/1992 | Boesch et al. |
| 5,254,330 A | 10/1993 | Ganderton et al. ........... 424/46 |
| 5,551,489 A | 9/1996 | Trofast et al. ............... 141/18 |
| 5,603,943 A | 2/1997 | Yanagawa .................. 424/434 |
| 5,695,744 A | 12/1997 | Neale et al. ................. 424/45 |
| 6,183,782 B1 * | 2/2001 | Hallworth |

FOREIGN PATENT DOCUMENTS

| GB | 1 242 211 | 8/1971 |
| GB | 1 381 872 | 1/1972 |
| GB | 1 402 423 | 8/1975 |
| GB | 1 410 588 | 10/1975 |
| GB | 1 478 020 | 6/1977 |
| GB | 1 569 611 | 6/1980 |
| GB | 1 571 629 | 7/1980 |
| GB | 0 398 631 | 11/1990 |
| WO | 87 05213 | 9/1987 |

* cited by examiner

Primary Examiner—Jyothsna Venkat
(74) Attorney, Agent, or Firm—Bacon & Thomas PLLC

(57) ABSTRACT

This invention relates to a pharmaceutical composition which is suitable for the administration of medicaments by inhalation. In particular, the pharmaceutical composition comprises microfine particles of medicament and at least one lactose pellet having a diameter of from about 10 to about 1500 micrometers, which pellet comprises a plurality of microfine lactose particles. A method of treating respiratory disorders which comprises administration by inhalation of an effective amount of medicament selected from the group consisting of anti-allergics, bronchodilators, anti-inflammatory steroids and mixtures thereof in the pharmaceutical composition as defined is described also.

17 Claims, No Drawings

INHALATION COMPOSITION CONTAINING LACTOSE PELLETS

This application is a continuation of application of U.S. application Ser. No. 08/702,700, filed Sep. 13, 1996, now U.S. Pat. No. 6,183,782, which is a 371 of PCT/EP95/00917, filed Mar. 13, 1995.

The present invention relates to an improved pharmaceutical composition, in particular a powder composition suitable for inhalation.

Numerous medicaments, especially those for the treatment of respiratory conditions such as asthma, are administered by inhalation. Since the drug acts directly on the target organ much smaller quantities of the active ingredient may be used, thereby minimising any potential side effects caused as a result of systemic absorption. The efficacy of this route of administration has been limited by the problems encountered in making appropriate and consistent dosages available to the lungs. The delivery systems currently available are pressurised metered dose inhalers, nebulisers and dry powder inhalers.

Metered dose inhalers require good coordination of actuation and inhalation in order to achieve consistent dose administration; this coordination may be difficult for some patients. Nebulisers are effective but are relatively expensive and bulky and as a result are mainly used in hospitals. A variety of dry powder inhalers have been developed and, since dry powder inhalers rely on the inspiratory effect of the patient to produce a fine cloud of drug particles, the coordination problems associated with the use of metered dose inhalers do not apply.

It has been found that medicaments for administration by inhalation should be of a controlled particle size in order to achieve maximum penetration into the lungs, preferably in the range of 1 to 10 micrometers in diameter. Unfortunately, powders in this particle size range, for example micronised powders, have a high bulk volume and have very poor flow characteristics due to the cohesive forces between the individual particles. These characteristics create handling and metering difficulties during manufacture of the medicament powder and, most importantly, adversely affect the accurate dispensing of the powder within the inhalation device. A number of proposals have been made in the literature to improve the fluidity of dry powder pharmaceutical formulations.

GB1520248 describes the preparation of soft pellets of finely powdered sodium cromoglycate which have satisfactory fluidity within the reservoir of the inhaler device but have sufficiently low internal coherence to break up into finer particles of medicament when introduced into the turbulent air stream in the mouthpiece of the device. Numerous other published patent applications suggest the use of carrier materials, for example GB1402423, particularly of coarser carriers with particles having sizes falling within a given range, for example GB1242211, GB1381872, GB1410588, GB1478020 and GB1571629. More recently WO87/05213 describes a carrier which comprises a conglomerate of one or more solid water-soluble diluents and a lubricant, EP-0260241 describes a lipid-based dry powder composition, and U.S. Pat. No. 5,143,126 describes a method of preparing flowable grain agglomerations of formoterol and lactose. Unfortunately the selection of the particle size of the drug and excipient and of the ratio of drug to excipient inevitably involves a compromise between adequate bulk and flow properties for metering and the desired redispersability of fine particle drug in the inhaled air flow.

According to the present invention there is provided a pharmaceutical powder composition suitable for inhalation which comprises microfine particles of medicament and at least one lactose pellet having a diameter of from about 10 to about 1500 micrometers, which pellet comprises a plurality of microfine lactose particles.

The particle size of the "microfine" particles of medicament and lactose should be such as to permit substantially all of the particles to be potentially available for inhalation into the lungs upon administration of the powder composition. Thus, for example, at least 90%, preferably at least 95% by weight of the particles will have a diameter of less than 15 micrometers, preferably in the range of 1 to 10 micrometers, for example 1 to 5 micrometers.

Medicaments which may be administered in the powder compositions according to the invention include any drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament.

Particularly preferred medicaments for administration using powder compositions in accordance with the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or as the sulphate salt), salmeterol (e.g. as the xinafoate salt), terbutaline (e.g. as the sulphate salt), reproterol (e.g. as the hydrochloride salt), beclomethasone dipropionate (e.g. as the monohydrate), fluticasone propionate or (−)-4-amino-3,5-dichloro-α-[[[6-[2-(2-pyridinyl)ethoxy]hexyl]amino] methyl]benzenemethanol. Salmeterol, salbutamol, fluticasone propionate, beclomethasone dipropionate and physiologically acceptable salts and solvates thereof are especially preferred.

It will be appreciated by those skilled in the art that the powder compositions according to the invention may, if desired, contain a combination of two or more active ingredients. Medicaments may be selected from suitable combinations of the medicaments mentioned hereinbefore. Thus, suitable combinations of bronchodilatory agents include ephedrine and theophylline, fenoterol and ipratropium, and isoetharine and phenylephrine formulations.

Other powder compositions may contain bronchodilators such as salbutamol (e.g. as the free base or as the sulphate salt), salmeterol (e.g. as the xinafoate salt) or isoprenaline in combination with an antiinflammatory steroid such as a beclomethasone ester (e.g. the dipropionate) or a fluticasone ester (e.g. the propionate) or a bronchodilator in combination with an antiallergic such as cromoglycate (e.g. the sodium salt). Combinations of isoprenaline and sodium cromoglycate, salmeterol and fluticasone propionate, or salbutamol and beclomethasone dipropionate as especially preferred.

The final powder composition desirably contains 0.1 to 90% w/w, preferably 0.5 to 75% w/w, especially 1–50% w/w, of medicament relative to the weight of the lactose pellets.

The internal strength or coherence of the lactose pellets of use in the present invention may be high ("hard" lactose pellets) or low ("soft" lactose pellets) or a mixture of "hard" and "soft" pellets. However, a preferred embodiment of the invention contains "soft" lactose pellets with a low internal coherence. These lactose pellets are friable and have an internal coherence such that the pellets remain substantially intact under conditions of packaging, transport, storage and when fluidised within a container in the inhalation device from which it is intended to dispense the composition according to the invention e.g. unit dose container or bulk reservoir and yet may be disrupted into independent microfine lactose particles upon egress into the turbulent air stream within the mouthpiece of the inhaler device. The coherence or strength of the pellets may be determined by methods known to those skilled in the art, for example by a simple strength test such as that described in GB1520247. Preferred lactose pellets have a crushing weight of between 50 and 500 mg, preferably between 50 and 200 mg, especially between 50 and 100 mg, when measured in accordance with the crushing test described herein.

The lactose pellets optionally contain one or more conventional pharmaceutically acceptable ingredients such as diluents, binders, solvents, surfactants, colouring and flavouring agents. However, the lactose pellets preferably consist essentially of microfine lactose particles.

The lactose pellets may be prepared by dry or wet pelleting methods known in the art. Thus, for example, microfine lactose particles may be dry pelleted using a tumbling or agitation process known as "balling", for example as described in U.S. Pat. No. 5,143,126. Alternatively, microfine lactose particles may be wet pelleted by tumbling in a container together with a minimal amount of liquid (see for example, review by C. Orr (1966), Particulate Technology, Chapter 9, published McMillan, New York). Suitable liquids wet the lactose particles adequately without dissolving them and have a sufficiently low boiling point to ensure rapid evaporation from the pellets thus formed and may be selected from, for example, alkanes, halogenated alkanes, alcohols, esters and ethers. Suitable liquids include, for example cyclohexane, n-hexane, chloroform, methylene chloride, CFC-113, methanol, ethanol, isopropanol, ethyl acetate and acetone and mixtures thereof. Lactose pellets may also be prepared, for example by controlled agglomeration in a fluidised bed or by spray drying a slurry of the lactose particles.

The preparation and storage of lactose pellets is desirably carried out under anhydrous conditions to obviate any adverse effects of free moisture on the strength of the lactose pellets. Lactose is generally utilised in the form of its monohydrate, which solvate contains approximately 5% w/w bound water. Desirably, the lactose pellets are substantially free of unbound water (free moisture), for example containing less than 1%, particularly less than 0.1% by weight of unbound water. The use of anhydrous lactose particles may be preferred.

Once formed, the lactose pellets may be admixed with microfine particles of one or more medicaments, optionally together with one or more conventional pharmaceutically acceptable ingredients, using conventional techniques to prepare the powder compositions according to the invention.

In one preferred embodiment of the invention the microfine medicament particles are coated onto the lactose pellets while tumbling, either as a fine powder, liquid suspension or solution of medicament. Coating with a liquid suspension of medicament particles by a process known as "layering" is preferred. Thus, the lactose pellets may be tumbled with a dispersion of microfine medicament particles in a suitable low boiling point, non-solubilising liquid, such as an alkane, halogenated alkane, alcohol, ester or ether. Suitable liquids will vary according to the medicament used but may include, for example, cyclohexane, n-hexane, chloroform, methylene chloride, CFC-113, methanol, ethanol, isopropanol, ethyl acetate and acetone and mixtures thereof.

Suitably a low wetting volume, for example 0.6:1 v/w liquid: medicament powder is employed in the layering process to prepare coated pellets. However, such concentrated suspensions of certain medicament and liquid combinations may be too viscous to be layered in this manner and it may be necessary and/or desirable to prepare coated pellets by continuous or intermittent spraying of a more dilute medicament suspension onto the lactose pellets under conditions of controlled evaporation. Alternatively, the lactose pellets may be slurried or sprayed with a suspension of medicament in a suitable non-solubilising liquid, followed by evaporation of the liquid to provide medicament-coated lactose pellets.

For all layering processes it is desirable to restrict the size range of the core pellets and hence it may be advantageous to pass the lactose pellets through one or more sieves to remove over or under-size pellets before layering with medicament. Desirably the lactose pellets have a diameter within the range of 50 to 1000 micrometers, particularly 150 to 1000 micrometers, for example in the range of 200 to 800 micrometers.

In an alternative embodiment the micronised medicament particles may be pelleted by methods known or analogous to methods known in the art. After pelleting, the medicament pellets may be admixed with the lactose pellets to provide a powder composition according to the invention which comprises at least one medicament pellet comprising a plurality of microfine medicament particles and at least one lactose pellet comprising a plurality of microfine lactose particles, each of said pellets having a diameter of from about 50 to about 1500 micrometers.

The powder compositions according to the invention optionally contain one or more conventional pharmaceutically acceptable ingredients such as diluents and flavouring agents. The particle size of any such ingredients will preferably be such as to substantially prevent their inhalation into the bronchial system upon administration of the powder composition, desirably in the range of 50 to 1000 micrometers.

The final powder composition desirably contains 0.1 to 90% w/w, preferably 1 to 20% w/w of medicament and 10 to 99.9% w/w, preferably 50 to 99% w/w of lactose pellets.

It is important that the powder compositions according to the invention are manufactured, packed and stored under substantially anhydrous conditions. Preferably the powder compositions contain less than 1%, especially less than 0.1% w/w of unbound water.

The compositions according to the invention may conveniently be filled into a bulk storage container, such as a multi-dose reservoir, or into unit dose containers such as capsules, cartridges or blister packs, which may be used with an appropriate inhalation device, for example as described in GB2041763, WO91/13646, GB1561835, GB2064336, GB2129691 or GB2246299. Such inhalers which contain a composition according to the invention are novel and form a further aspect of the invention. The compositions of the invention are particularly suitable for use with multi-dose reservoir-type inhaler devices in which the composition is metered e.g. by volume from a bulk powder container into aose-metering cavities. The lower limit of powder delivery which may be accurately metered from a multi-dose reservoir-type inhaler device is in the region of 100 to 200 micrograms. The formulations of the present invention are therefore particularly advantageous for highly potent and hence low dose medicaments which require a high ratio of excipient for use in a multi-dose reservoir-type inhaler device.

Dry powder inhalers are designed to deliver a fixed unit dosage of medicament per actuation, for example in the range of 10 to 5000 micrograms medicament per actuation, preferably 25 to 500 micrograms.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicament are employed the dose of each component of the combination will in general be that employed for each component when used alone. Typically, administration may be one, or more times, for example from 1 to 8 times per day, giving for example 1, 2, 3 or 4 unit doses each time.

Thus, for example, each actuation may deliver 25 micrograms salmeterol, 100 micrograms salbutamol, 25, 50, 125 or 250 micrograms fluticasone propionate or 50, 100, 200 or 250 micrograms beclomethasone dipropionate.

Crushing Test

A number of tests for the friability (strength or internal coherence) of pellets or granules have been described in the literature, see for example GB1520247 and Ganderton & Hunter (1971), J. Pharm. Pharmacol 23, Suppl. 1S–10S, and instrumentation specifically devised for this purpose is now available, for example from Etewe GmbH, Karlsruhe. A simple method was devised and used to assess the crushing weight of pellets according to the invention.

Thus, a single pellet was placed on a marked centre position on a base slide and viewed from above through a stereomicroscope. Microscopy glass coverslips were used as weights, either 22 mm square (mean 170 mg, SD 4 mg) or 16 mm circular (mean 75 mg, SD 4 mg). The first weight was supported at one side and released by sliding the support away laterally. Any free-fall was minimised by standardising the pellet diameter. When a single weight did not fracture or crush the pellet, further weights were applied sequentially.

Weak pellets characteristically showed crushing of the upper surface and a sharp diametric break, at mean crushing weights of less than 500 mg, preferably less than 250 mg.

The invention is illustrated by the following examples.

EXAMPLE 1

Lactose Pellets

Micronised lactose monohydrate (2 g) was placed in a tubular glass screw-cap scintillation vial and acetone (1.2 ml) was applied to the headspace walls to avoid localised overwetting. The vial was capped immediately and rotated by hand at 45° to the vertical to give suitable powder flow to induce balling. An occasional sharp tap on the bench was needed to dislodge powder adhering to the vial or forming large agglomerates. As soon as all free powder had disappeared the pellets were immediately stored over silica gel.

EXAMPLE 2

Lactose Pellets

Micronised lactose monohydrate (50 g) was placed in a cylindrical glass pelletising pan of 160 mm diameter and 80 mm depth, tapering towards entry, with an axial driving spindle mounted on the flat base. The pan was mounted in the driving chuck of an electric motor at 45° to the vertical and run at 30 rpm (peripheral angular velocity=0.25 ms$^{-1}$). This arrangement gave the required flow pattern in which the powder climbed and then flowed down over a wide region of the flat base of the pan. A coarse liquid spray of CFC-113 (30 ml) was generated with a "Polyspray 2" (Hozelock) spray gun after pressurising the tank initially with 60 actuations of the hand air pump. The pellets were tumbled for 5 minutes in the closed pan and then immediately stored over silica gel.

EXAMPLE 3

Coated Lactose Pellets

Lactose pellets prepared according to Example 2 were sieved through stainless steel sieves to provide a fraction of pellet size 355–500 µm. Sieved lactose pellets (2 g) were mixed with micronised salmeterol xinafoate (100 mg) and then the mixture was placed in a scintillation vial. CFC-113 (60 µl) was applied to the headspace walls, the mixture tumbled as described in Example 1, air dried for 2 minutes and the pellets were immediately stored over silica gel. The oversize fractions (>500 µm) were removed by sieving.

The drug was determined to be uniformly distributed and the layered pellets were weak as required and gave good respirable drug delivery i.e. redispersion when tested e.g. for delivery from a Turbohaler inhalation device as measured by the twin impinger assay. As used herein reference to the "twin impinger assay" means "Determination of the deposition of the emitted dose in pressurised inhalations using Apparatus A" as defined in British Pharmacopaeia 1988, pages A204–207, Appendix XVIIC.

EXAMPLES 4 TO 6

Lactose Pellets

Lactose pellets were prepared as described in Example 1 using either cyclohexane, acetone or CFC-113: absolute ethanol (50:50 v/v) in place of CFC-113.

EXAMPLE 7

Lactose Pellets

Micronised lactose monohydrate (approx 5 g) was shaken by hand over a 710 μm aperture sieve to produce friable lactose pellets.

EXAMPLE 8

Lactose Pellets

Micronised lactose monohydrate (1 g) was tumbled in a rotating glass vial for 20 minutes to produce friable lactose pellets (42% in sieve range 250–710 μm).

What is claimed is:

1. A pharmaceutical powder composition suitable for inhalation comprising microfine particles of medicament and at least one preformed lactose pellet having a diameter of from about 10 to about 1500 micrometers, which pellet comprises a plurality of microfine lactose particles, wherein at least about 90% by weight of the microfine particles of lactose have a diameter of less than about 15 micrometers, and wherein the medicament is selected from the group consisting of codeine, dihydromorphine, ergotamine, fentanyl, morphine, diltiazem, cromoglycate, ketotifen, nedocromil, cephalosporins, penicillins, streptomycin, sulphonamides, tetracyclines, pentamidine, methapyrilene, budenoside, flunisolide, tipredane, triamcinolone acetonide, noscapine, ephedrine, adrenaline, fenoterol, formoterol, isoprenaline, metaproterenol, phenylephrine, phenylpropenolamine, pirbuterol, reproterol, rimeterol, terbutaline, isoetharine, tulobuterol, orciprenaline, (−)-4-amino-3,5-dichloro-a-[[[6-[-2-(2-pyridinyl)ethoxy]hexyl]-amino]methyl] benzenemethanol, amiloride, ipratropium, atropine, oxitropium, cortisone, hydrocortisone, prednisolone, aminophylline, choline theophyllinate, lysine theophyllinate, theophylline, salmeterol xinafoate, salbutamol sulfate, fluticasone propionate glucagon and any mixtures thereof.

2. A pharmaceutical powder composition according to claim 1 wherein said at least one lactose pellet has a diameter of from about 150 to 1000 micrometers.

3. A pharmaceutical powder composition according to claim 1 wherein said at least one lactose pellet is hard or soft.

4. A pharmaceutical powder composition according to claim 3 wherein the soft lactose pellet has a crushing weight of about 50 to about 500 mg.

5. A pharmaceutical powder composition according to claim 4 wherein the soft lactose pellet has a crushing weight of about 50 to about 100 mg.

6. A pharmaceutical powder composition according to claim 1, wherein the medicament is terbutaline.

7. A pharmaceutical powder composition according to claim 1 wherein the medicament is formoterol.

8. A pharmaceutical powder composition according to claim 1, wherein the medicament is budenoside.

9. A pharmaceutical composition according to claim 1, wherein the microfine particles of medicament form at least one medicament pellet.

10. A process for preparing a pharmaceutical composition according to claim 1 comprising admixing microfine particles of medicament with at least one lactose pellet having a diameter of from about 10 to about 1500 micrometers, which pellet comprises a plurality of microfine lactose particles.

11. A process according to claim 10, wherein the admixing comprises coating the lactose pellets with a liquid suspension or solution of medicament.

12. An inhalation device comprising a composition according to claim 1.

13. A method of treating respiratory disorders which comprises administration by inhalation of an effective amount of a pharmaceutical powder composition according to claim 1 group consisting of anti-allergics, bronchodilators, anti-inflammatory steroids and mixtures thereof and at least one lactose pellet having a diameter of from about 10 to about 1500 micrometers, which pellet comprises a plurality of microfine lactose particles, and wherein at least about 90% by weight of the microfine particles of lactose have a diameter of less than about 15 micrometers.

14. A pharmaceutical powder composition according to claim 4 wherein the medicament is selected from the group consisting of salmeterol xinafoate, salbutamol sulphate and fluticasone propionate.

15. A pharmaceutical powder composition according to claim 5 wherein the medicament is selected from the group consisting of salmeterol xinafoate, salbutamol sulphate and fluticasone propionate.

16. A pharmaceutical powder composition according to claim 1 wherein said at least one lactose pellet has a diameter form about 150 to 1000 micrometers and wherein at least about 90% byway of the microfine particles of lactose have a diameter of less than about 15 micrometers and wherein the lactose pellet is a soft lactose pellet having a crushing weight of about 50 to about 150 mg.

17. A pharmaceutical powder composition according to claim 16, wherein the soft lactose pellet has a crushing weight of about 50 to about 100 mg.

* * * * *